United States Patent [19]
Song et al.

[11] Patent Number: 5,843,998
[45] Date of Patent: Dec. 1, 1998

[54] SKIN BLEMISH TREATMENT

[76] Inventors: Jin Song, 2316 Woodfield Way, Bedford, Tex. 76021; John Koch, 8343 Deep Green Dr., Dallas, Tex. 75249; Marilyn Squier, 614 Reinosa, Garland, Tex. 75043

[21] Appl. No.: 884,801

[22] Filed: Jun. 30, 1997

[51] Int. Cl.⁶ .......................... A61K 31/17; A61K 31/60; A61K 31/19
[52] U.S. Cl. .......................... 514/588; 514/159; 514/557; 514/859
[58] Field of Search .................. 514/588, 557, 514/159, 859

[56] References Cited

U.S. PATENT DOCUMENTS

| | | | |
|---|---|---|---|
| 4,607,101 | 8/1986 | Berstein | 514/24 |
| 4,895,727 | 1/1990 | Allen | 424/642 |
| 5,110,801 | 5/1992 | Leveen et al. | 514/34 |

OTHER PUBLICATIONS

Handbook of Nonprescription Drugs 5th Ed. Penna et al. 1977.

*Primary Examiner*—Kevin E. Weddington
*Attorney, Agent, or Firm*—David W. Carstens; Carstens, Yee & Cahoon, LLP.

[57] ABSTRACT

A skin blemish treatment combines a base with therapeutically effective amounts of carbamide peroxide and alpha-hydroxy acid ("AHA"). The resulting formulation effectively treats human acne vulgaris while exhibiting none of the severe adverse side effects associated with benzoyl peroxide. The AHA can be any synthetic or naturally occurring alpha-hydroxy acid. Salicylic acid can augment the composition, as can an anti-inflammatory such as allantoin. Fragrance, coloring agents, and preservatives can also be added.

22 Claims, No Drawings

SKIN BLEMISH TREATMENT

TECHNICAL FIELD OF THE INVENTION

The present invention relates generally to a skin blemish treatment and more specifically to a formulation that contains carbamide peroxide and one or more alpha-hydroxy acids. This formulation proves effective without the toxic effects of formulations containing benzoyl peroxide.

BACKGROUND OF THE INVENTION

Acne vulgaris is an inflammatory disease of the pilosebaceous glands characterized by an eruption of the skin, often pustular in nature but not suppurative. Acne is a common affliction of the adolescent and affects a small but significant percentage of the adult population. Acne lesions are of four basic types: comedones (blackheads or whiteheads), papules, pustules, and cysts (or nodules). Various topical agents are utilized in the treatment of acne and these include sulfur, resorcinol, salicylic acid, benzoyl peroxide, vitamin A acid, carbamide peroxide, and topical antibiotics. Acne involvement results in unsightly lesions, particularly on the face, and in some cases results in severe scarring.

There are a variety of methods for treating acne vulgaris including topically applying various scrubbing or abrasive compositions, topically applying deep cleaning or astringent compositions and also exposure to ultraviolet radiation.

U.S. Pat. No. 4,607,101 claims the use of Urea Peroxide (carbamide peroxide), a known disinfectant, in the treatment of acne vulgaris through a topically administered form at a dosage level considered to effective, which is greater than or equal to one percent by volume of the carrier. The carbamide peroxide can be further combined with a topical antibiotic, nicotinic acid or nicotinamide.

Alpha-hydroxy acids (AHA) are well documented for use in both skin peels and cell turnover preparations. Their action is to diminish the thickness of the stratum corneum thus improving the skin surface rendering it more flexible. Follicular hyperkeratinization of keratosis pilaris and acneiform comedones responds well to topical AHA/s. Treatment of the former is with cream formulations and concentrations as used for dry skin. Applications are continued twice daily until all follicular imperfections are dislodged, and thereafter as needed to maintain follicular orifices open. For treatment of comedones of acne, liquid or gel vehicles are preferable to creams.

Salicylic acid (2-hydroxy benzoic) an aromatic acid, is recognized as an effective treatment for acne; "Specifically, the agency has determined that the only ingredients that meet monograph conditions are salicylic acid, sulfur, and resorcinol and resorcinol monoacetate (in combination products)," (Federal Register/Vol 56, No. 159/Friday, Aug. 16, 1991, page 41019) from 0.5% to 2% by weight (Federal Register/Vol 56, No. 159/Friday, Aug. 16, 1991, page 41020).

Benzoyl peroxide, which contains a benzene ring, is recognized as one of the most effective treatments for acne. However, benzoyl peroxide is very toxic, and its known side effects include tumor promotion, extreme dryness, itching, irritation, erythema, peeling or swelling in the skin.

A need exists for a treatment for human acne vulgaris that approaches or exceeds the effectiveness of, yet avoids the disadvantages of, benzoyl peroxide.

SUMMARY OF THE INVENTION

The present invention relates to a blemish treatment that combines a base, carbamide peroxide, and one or more alpha-hydroxy acids. The base can be any pharmaceutically-accepted base including glycerin, glycol, alcohol, or cellulose-derived gum, or thickener. For example, glycerin or glycol are suitable bases that also act as moisturizers by virtue of being humectants. The carbamide peroxide is a compound well-recognized in the art as an effective treatment for acne vulgaris although, by itself, is not generally as effective as benzoyl peroxide. In an alternative embodiment, the carbamide peroxide may be replaced with hydrogen peroxide. Finally, the alpha-hydroxy acid ("AHA") can be any combination of synthetic and naturally-occurring AHA, including malic acid, tartaric acid, glycolic acid, and lactic acid. In combination with carbamide peroxide, AHA approaches the effectiveness of benzoyl peroxide without the harsh and potentially carcinogenic side effects of benzoyl peroxide.

In addition to these three basic elements, the formulation can be augmented with other ingredients which have proven beneficial effects on the skin. For example, allantoin can be included to act as an anti-inflammatory and healing agent. Salicylic acid can be added as an additional acne treatment component. Other ingredients such as fragrance, color, and preservative may also be added. For each example given, a number of other ingredients could be substituted. The final formulation though, has the benefits of a relatively high effectiveness rate without the carcinogenic and other undesirable side effects of benzoyl peroxide.

DETAILED DESCRIPTION OF THE INVENTION

The present composition for treatment of human acne vulgaris overcomes many of the disadvantages found in the prior art. As discussed above, the formulation consists of three basic ingredients: a base, carbamide peroxide, and at least one alpha-hydroxy acid. The base can be any pharmaceutically acceptable base, or a combination thereof. The preferred bases are glycerin, glycol, alcohol, and cellulose gum. The base represents between 58% to 98.45% of the formulation.

The carbamide peroxide (urea peroxide) is a known disinfectant that kills acne-causing bacteria and drys fatty acids and esters from the skin. Acting alone, carbamide peroxide is not as effective as benzoyl peroxide in the treatment of acne vulgaris. Carbamide peroxide, the chemical formula of which is

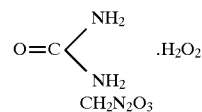

$CH_2N_2O_3$ does not contain a benzene ring and thus does not cause the toxic side effects associated with compounds, such as benzoyl peroxide, that do contain a benzene ring. Carbamide peroxide represents 1.0% to 25.0% by volume of the present invention.

The preferred composition is approximately 10% carbamide peroxide, 0.35% alpha-hydroxy acid, and 89.65% base. The alpha-hydroxy acid in the preferred composition is a combination of lactic acid, citric acid, and tartaric acid; it is conceived, however, that any combination of one or more alpha-hydroxy acids will enhance the effectiveness of carbamide peroxide in the treatment of acne vulgaris.

A series of tests have been performed, the results of which demonstrate the effectiveness of the present composition. In the acne reduction comparison study, four sample groups of acne patients, Groups I–IV, participated. The demographics of each group is set forth, respectively, in Tables 1.2, 2.2, 3.2, and 4.2. In the study, one of the four sample compositions was applied to the face of acne patients twice daily for six weeks. For comparison purposes, the patients in Group IV applied a commercial preparation containing 10% benzoyl peroxide. The results for Group IV are shown in Table 4.1. As a group, Group IV subjects showed no improvement in acne symptoms after two weeks, a mean 50% improvement after 4 weeks, and a mean 60% improvement after 6 weeks.

As discussed above, salicylic acid may be added to the invention. Salicylic acid represents between 0.5% to 2.0% of the present composition. While not the preferred embodiment, an alternative embodiment of the composition is approximately 10% carbamide peroxide, 0.35% alpha-hydroxy acid, 1% salicylic acid, and 88.65% base. As demonstrated in Table 1.1 below, the effectiveness of this composition approaches that of a formulation containing 10% benzoyl peroxide (see Table 4.1), but results are seen sooner. Table 1.1 demonstrates the application of Group I of a composition consisting of 10% carbamide peroxide, 0.35% alpha-hydroxy acid, and 1% salicylic acid in a pharmaceutically acceptable base. After 2 weeks, the Group I patients exhibited a mean 25.0% reduction in acne symptoms. Thus, as a group, the Group I patients experienced a reduction in acne symptoms faster than the Group IV patients. After 4 weeks, the mean effectiveness of the Group I and Group IV preparations was the same - 50%. After 6 weeks, the mean improvement for Group I remained at 50%. Thus, the Group I composition approached the effectiveness level of benzoyl peroxide, but results were noted more quickly. Group I patients reported no adverse side effects.

Table 2.1 demonstrates the results of application of the preferred embodiment of the present composition. The Group II composition consisted of 10% carbamide peroxide, 0.35% alpha-hydroxy acids, and 89.65% base. No salicylic acid was introduced in the preferred composition. As with the Group IV benzoyl peroxide composition, the Group II composition engendered no discernable effect after two weeks. After 4 weeks, however, the effectiveness of the Group II composition surpassed that of benzoyl peroxide, with a mean improvement of 55.6%. After 6 weeks, the Group II composition resulted in a mean improvement of 88.9% reduction in acne symptoms. Compared with the week 6 result in Table 4.1 (60%), the Group II 6 week result of 88.9% demonstrates a clearly vast improvement over the benzoyl peroxide results. Group II patients reported no adverse side effects.

Table 3.1 demonstrates the limited effectiveness of a composition of two known treatment agents, salicylic acid and alpha-hydroxy acid, without the addition of carbamide peroxide. The Group III patients experienced no noticeable improvement in acne symptoms for the first four weeks of the test, and experienced only a mean reduction of 20% in symptoms after 6 weeks. Thus, the present composition has been shown to be significantly more effective than a formulation containing alpha-hydroxy acid and salicylic acid, but no carbamide peroxide.

Fragrance, coloring agent, and/or preservative can be added to the present composition. Also, a healing agent, such as allantoin, may be added, as may an anti-inflammatory. In an alternative embodiment, hydrogen peroxide may replace the carbamide peroxide.

ACNE REDUCTION COMPARISON STUDY

TABLE 1.1

| | Compound Containing 10% Carbamide Peroxide, .35% AHA, 1% Salicylic Acid | | | | | | | |
|---|---|---|---|---|---|---|---|---|
| Subject | B-5382 PRE | B-5382 2 WKS | B-5382 4 WKS | B-5382 6 WKS | UNTRT PRE | UNTRT 2 WKS | UNTRT 4 WKS | UNTRT 6 WKS |
| 1 | 3.0 | 2.0 | 1.0 | 1.0 | 3.0 | 3.0 | 3.0 | 3.0 |
| 2 | 2.0 | 1.0 | 1.0 | 1.0 | 2.0 | 2.0 | 2.0 | 2.0 |
| 3 | 2.0 | 1.0 | 1.0 | 1.0 | 2.0 | 2.0 | 2.0 | 2.0 |
| 4 | 2.0 | 2.0 | 1.0 | 1.0 | 1.0 | 1.0 | 1.0 | 1.0 |
| 5 | 3.0 | 3.0 | 2.0 | 2.0 | 3.0 | 3.0 | 3.0 | 3.0 |
| MEAN | 2.4 | 1.8 −25.0% | 1.2 −50.0% | 1.2 −50.0% | 2.2 | 2.2 | 2.2 | 2.2 |

TABLE 1.2

| GROUP I | |
|---|---|
| Number of subjects enrolled | 5 |
| Number of subjects completing study | 5 |
| Age Range | 16–29 |
| Sex | |
| Male | 2 |
| Female | 3 |
| Race | |
| Caucasian | 4 |
| Hispanic | 1 |

TABLE 2.1

Compound Containing 10% Carbamide Peroxide and .35% AHA (no salicylic acid)

| Subject | B-5383 PRE | B-5383 2 WKS | B-5383 4 WKS | B-5383 6 WKS | UNTRT PRE | UNTRT 2 WKS | UNTRT 4 WKS | UNTRT 6 WKS |
|---|---|---|---|---|---|---|---|---|
| 1 | 2.0 | 2.0 | 1.0 | 0.0 | 2.0 | 2.0 | 2.0 | 2.0 |
| 2 | 3.0 | 3.0 | 2.0 | 1.0 | 3.0 | 3.0 | 3.0 | 3.0 |
| 3 | 2.0 | 2.0 | 1.0 | 0.0 | 2.0 | 2.0 | 2.0 | 2.0 |
| 4 | 1.0 | 1.0 | 0.0 | 0.0 | 1.0 | 1.0 | 1.0 | 1.0 |
| 5 | 1.0 | 1.0 | 0.0 | 0.0 | 1.0 | 1.0 | 1.0 | 1.0 |
| MEAN | 1.8 | 1.8 0.0% | 0.8 −55.6% | 0.2 −88.9% | 1.8 | 1.8 | 1.8 | 1.8 |

TABLE 2.2

| GROUP II | |
|---|---|
| Number of subjects enrolled | 5 |
| Number of subjects completing study | 5 |
| Age Range | 16–37 |
| Sex | |
| Male | 0 |
| Female | 5 |
| Race | |
| Caucasian | 5 |

TABLE 3.1

Compound Containing .35% AHA and 1% Salicylic Acid (no carbamide peroxide)

| Subject | B-5384 PRE | B-5384 2 WKS | B-5384 4 WKS | B-5384 6 WKS | UNTRT PRE | UNTRT 2 WKS | UNTRT 4 WKS | UNTRT 6 WKS |
|---|---|---|---|---|---|---|---|---|
| 1 | 3.0 | 3.0 | 3.0 | 3.0 | 3.0 | 3.0 | 3.0 | 3.0 |
| 2 | 3.0 | 3.0 | 3.0 | 2.0 | 3.0 | 3.0 | 3.0 | 3.0 |
| 3 | 2.0 | 2.0 | 2.0 | 2.0 | 2.0 | 2.0 | 2.0 | 2.0 |
| 4 | 1.0 | 1.0 | 1.0 | 1.0 | 1.0 | 1.0 | 1.0 | 1.0 |
| 5 | 1.0 | 1.0 | 1.0 | 0.0 | 1.0 | 1.0 | 1.0 | 1.0 |
| MEAN | 2.0 | 2.0 0.0% | 2.0 0.0% | 1.6 −20.0% | 2.0 | 2.0 | 2.0 | 2.0 |

TABLE 3.2

| GROUP III | |
|---|---|
| Number of subjects enrolled | 5 |
| Number of subjects completing study | 5 |
| Age Range | 16–42 |
| Sex | |
| Male | 4 |
| Female | 1 |
| Race | |
| Caucasian | 5 |

TABLE 4.1

Commercial Preparation Containing 10% Benzoyl Peroxide

| Subject | B-5385 PRE | B-5385 2 WKS | B-5385 4 WKS | B-5385 6 WKS | UNTRT PRE | UNTRT 2 WKS | UNTRT 4 WKS | UNTRT 6 WKS |
|---|---|---|---|---|---|---|---|---|
| 2 | 2.0 | 2.0 | 1.0 | 1.0 | 2.0 | 2.0 | 2.0 | 2.0 |
| 3 | 2.0 | 2.0 | 1.0 | 1.0 | 2.0 | 2.0 | 2.0 | 2.0 |
| 4 | 2.0 | 2.0 | 1.0 | 0.0 | 2.0 | 2.0 | 2.0 | 2.0 |
| 5 | 2.0 | 2.0 | 1.0 | 1.0 | 2.0 | 2.0 | 2.0 | 2.0 |
| MEAN | 2.0 | 2.0 | 1.0 | 0.8 | 2.0 | 2.0 | 2.0 | 2.0 |
|  |  | 0.0% | −50.0% | −60.0% |  |  |  |  |

TABLE 4.2

| GROUP IV | |
|---|---|
| Number of subjects enrolled | 5 |
| Number of subjects completing study | 5 |
| Age Range | 16–37 |
| Sex | |
| Male | 0 |
| Female | 4 |
| Race | |
| Caucasian | 2 |
| Hispanic | 1 |
| Asian | 1 |

We claim:

1. A composition suitable for treating acne vulgaris in humans comprising:
   (a) a therapeutically effective amount of carbamide peroxide;
   (b) a therapeutically effective amount of one or more alpha-hydroxy acids; and
   (c) a base.

2. The composition of claim 1 further comprises a therapeutically effective amount of salicylic acid.

3. The composition of claim 1 further comprises a therapeutically effective amount of an anti-inflammatory.

4. The composition of claim 1 wherein said base is selected from an alcohol, glycerin, glycol, or cellulose gum or mixtures thereof.

5. The composition of claim 1 further comprises a fragrance.

6. The composition of claim 1 further comprises a preservative.

7. The composition of claim 1 further comprises a coloring agent.

8. The composition of claim 1 wherein said carbamide peroxide is present in the range from 1.0% to 25% by volume.

9. The composition of claim 1 wherein said alpha-hydroxy acid is present in the range from 0.05% to 15.0% by volume.

10. The composition of claim 2 wherein said salicylic acid is present in the range from 0.5% to 2.0% by volume.

11. The composition of claim 1 wherein said alpha-hydroxy acid comprises a synthetic alpha-hydroxy acid.

12. The composition of claim 1 wherein said alpha-hydroxy acid is one or more naturally-occurring alpha-hydroxy acids.

13. The composition of claim 12 wherein said alpha-hydroxy acid is tartaric acid.

14. The composition of claim 12 wherein said alpha-hydroxy acid is glycolic acid.

15. The composition of claim 12 wherein said alpha-hydroxy acid is malic acid.

16. The composition of claim 12 wherein said alpha-hydroxy acid is lactic acid.

17. The composition of claim 3 wherein said healing agent is allantoin.

18. A method of manufacturing a blemish control lotion comprising the steps of:
   (a) mixing a base with a therapeutically effective amount of carbamide peroxide; and
   (b) adding a therapeutically effective amount of alpha-hydroxy acid.

19. The method of claim 18 further comprises (c) adding a therapeutically effective amount of salicylic acid.

20. The method of claim 18 wherein said amount of carbamide peroxide is in the range from 1.0% to 25% by volume.

21. The method of claim 18 wherein said amount of alpha-hydroxy acid is in the range from 0.05% to 15.0% by volume.

22. The method of claim 19 wherein said amount of salicylic acid is in the range of 0.5% to 2.0% by volume.

* * * * *